(12) United States Patent
Bray

(10) Patent No.: US 6,523,418 B2
(45) Date of Patent: *Feb. 25, 2003

(54) APPARATUS AND METHOD FOR ULTRASONIC STRESS MEASUREMENT USING THE CRITICALLY REFRACTED LONGITUDINAL ($L_{CR}$) ULTRASONIC TECHNIQUE

(76) Inventor: Don E. Bray, P.O. Box 10315, College Station, TX (US) 77842-0315

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/573,053

(22) Filed: May 16, 2000

(65) Prior Publication Data

US 2002/0078759 A1 Jun. 27, 2002

Related U.S. Application Data

(63) Continuation-in-part of application No. 09/234,157, filed on Jan. 19, 1999.
(60) Provisional application No. 60/094,648, filed on Jul. 30, 1998.

(51) Int. Cl.[7] ............................................. G01N 29/04
(52) U.S. Cl. ........................................... 73/801; 73/637
(58) Field of Search ........................ 73/778, 801, 618, 73/620, 622, 627, 628, 637

(56) References Cited

U.S. PATENT DOCUMENTS

| | | | |
|---|---|---|---|
| 3,720,098 A | 3/1973 | Dixon | |
| 4,398,421 A | 8/1983 | White | |
| 4,413,517 A | 11/1983 | Soden | |
| 4,453,410 A * | 6/1984 | Schmitz et al. | 73/640 |
| 4,458,534 A | 7/1984 | Kising | |
| 4,474,064 A * | 10/1984 | Naruse et al. | 73/622 |
| 4,522,071 A | 6/1985 | Thompson | |
| 4,577,507 A * | 3/1986 | Jestrich et al. | 73/640 |
| 4,926,692 A | 5/1990 | Brokowski | |
| 5,005,417 A * | 4/1991 | Kawasaki et al. | 73/593 |
| 5,007,291 A * | 4/1991 | Walters et al. | 73/640 |
| 5,016,200 A | 5/1991 | Passarelli | |
| 5,170,366 A | 12/1992 | Passarelli | |
| 5,398,551 A * | 3/1995 | Kawasaki et al. | 73/593 |
| 5,503,020 A | 4/1996 | Mandracchia | |

OTHER PUBLICATIONS

Hartford Stream Boiler Co., "The Hartford Wedge System for Dryer Roll Thickness Measurements.".
Hartford Stream Boiler Co., "The Hartford Wedge," (Aug. 21, 1982).
Sonic Force Corporation, "Railroad Rail Force (Stress) Measurements," (Aug. 21, 1982).

(List continued on next page.)

Primary Examiner—Max Noori
(74) Attorney, Agent, or Firm—Carstens Yee & Cahoon LLP; David W. Carstens

(57) ABSTRACT

The latent stress in both flat and curved materials can be measured using critically refracted longitudinal ultrasonic technique. The system uses a frame to hold a hydraulic piston. The piston is used to apply an adjustable force against the probes. A signal is initiated by a transmitting probe. The signal is angled against the piece under test so as to create a critically refracted wave along the piece. Wedge-shaped probe pads allow placement of the probes on both flat and curved surfaces with various radii and arc lengths. The delay time to receive the wave at a first and second receiving probe is measured. The delay time correlates to a stress in the piece.

12 Claims, 6 Drawing Sheets

OTHER PUBLICATIONS

Shaikh, Nisar, "Transducers and Techniques for Ultrasonic Nondestructive Evaluation of Structural Plastics," Review of Progress in Quantitative Nondestructive Evaluation, Plenum Press (New York), p. 1831–1835, (Apr. 21, 1992).

Leon–Salamanca, T. and Bray, D.F., "Residual Stress Measurement in Steel Plates and aWelds Using Critically Refracted Longitutdinal (Lcr) Waves," Research in Nondestructive Evaluation, Springer–Verlag (New York), p. 169–184, (Apr. 21, 1996).

Egle, D.M. and Bray, D.E., "Application of the Acousto–elastic Effect to Rail Stress Measurement," Materials Evaluation, (Mar. 21, 1979).

Egle, D.M. and Bray, D.E., "Nondestructive Measurement of Longitutdinal Rail Stresses; Application of the Acoustoelastic Effect to Rail Stress Measurement," DOT Report FRA/ORD–77/34.I, p. 113 pages, (Jan. 21, 1978).

Moskal, Max D., "Round Robin Evaluation of Gray Cast Iron Thickness Test Methods," TAPPI Proceedings, 1990 Engineering Conference, Seattle, WA, Sep. 24–27, 1990.

White, Dennis, "Examining Cast Iron Dryers and Determining Tensile Strength," TAPPI Proceedings, 1992 Engineering Conference, USA, 1992.

Pfluger, R., Bray, D.E., and Srinivasan, M., "Evaluation of Residual Stress Gradients in Ductile Cast Iron Using the Critically Refracted Longitudinal (Lcr) Wave Technique," Proceedings, International Chemical and Petroleum Industry Inspection Technology IV Topical Conference, Houston, TX, Jun. 19–22, 1995, pp. 255–258.

Stanley, Rod K., Nondestructive Evaluation, Revised Edition, Jan. 1997, CRC Press, Boca Raton, FL, U.S.A.

Bray, D.E., Tang, W. and Grewal, D.,, "Ultrasonic Stress Evaluation in a Turbine/Compressor Rotor," Journal of Testing and Evaluation, No. 5, Sep. 1997, pp. 503–509, vol. 25, U.S.A.

Bray, D. E., Pathak, N. and Srinivasan, M. N., "Residual Stress Mapping in a Steam Turbine Disk Using the LCr Ultrasonic Technique," Materials Evaluation, 1996, pp. 832–839, vol. 54, No. 7, U.S.A.

Bray, D.E. and Junghans, P.G., "Applications of the LCR Ultrasonic Technique for Evaluation of Post–Weld Heat Treatment in Steel Plates," NDT&E International, 1995, pp. 235–242, vol. 28, No. 4, U.S.A.

Srinivasan, M.N., Chundu, S.N., Bray, D.E., and Alagarsamy, A., "Ultrasonic Technique for Residual Stress Measurement in Ductile Iron Continuous Cast Round Bars," Journal of Test and Evaluation, Sep. 1992, pp. 331–335, vol. 20, No. 5, U.S.A.

Srinivasan, M.N., Chundu, S.N., Bray, D.E., and Alagarsamy, A., "Detection of Stress in Ductile Iron Bars Using Critically Refracted Longitudinal Wave Techniques," AFS (American Foundry Society) Transactions, 1992, pp. 309–312, vol. 92, No. 114, U.S.A.

Srinivasan, M., Bray, D.E., Junghans, P., and Alagarsamy, A., "Critically Refracted Longitudinal Wave Technique: A New Tool for the Measurement of Residual Stresses in Castings," AFS (American Foundrymen Society) Transactions, 1991, pp. 265–267, vol. 91, No. 157, U.S.A.

Bray, D.E. and Leon–Salamanca, T., "Zero–Force Travel–Time Parameters of Ultrasonic Head–Waves in Railroad Rail," Materials Evaluation, Jun. 1985, pp. 854–858, 863, vol. 43, No. 7, U.S.A.

Egle, D.M. and Bray, D.E., "Ultrasonic Measurement of Longitudinal Rail Stresses," Materials Evaluation, Mar. 1979, pp. 41–46, 55, vol. 378, No. 4, U.S.A.

Egle, D.M. and Bray, D.E., "Measurements of Acoustoelastic and Third Order Elastic Constants for Rail Steel," Journal of the Acoustical Society of America, Sep. 1976, pp. 741–744, vol. 60, No. 3, U.S.A.

Bray, Don E., Kim, S–J., and Fernandes, M., "Ultrasonic Stress Measurement in Aluminum Plates," To appear— Proceedings Ninth International Symposium on Nondestructive Characterization of Materials,Jun. 28–Jul. 2, 1999, Sydney, Australia.

Bray, Don E., and Chance, Brent, "Practical Aspects of Ultrasonic Stress Measurement," To appear–Proceedings 1999 ASME NDE Engineering Division Topical Conference, Apr. 20–22, 1999, San Antonio, TX.

Bray, Don E., Tang, Wei, Tittiman, Bernard, and Miyasaka, Chiaki, "Detecting Load Damage in Composite Materials using Ultrasonic Techniques," To appear–Proceedings 1999 ASME NDE Engineering Division Topical Conference, Apr. 20–22, 1999, San Antonio, TX.

Bray, Don E., "Ultrasonic Stress Measurements in Turbine Components," Proceedings of the 1998 International Joint Power Generation Conference—Power, Aug. 23–26, 1998, pp. 43–50, vol. 2, J. Legler, Ed., PWR–vol. 33, The American Society of Mechanical Engineers, Baltimore, MD.

Bray, Don E. and Srivivasan, M. N., "Near–Surface and Through–Thickness Residual Stress Evaluation in Ductile Iron Using the Critically Refracted Longitudinal Wave Technique," Presented at the ASME–ASIA '97 Congress & Exhibition, Sep. 30–Oct. 2, 1997 Paper No. 97–AA–68, Singapore.

Bray, Don E., and Dietrich, M., "Stress Evaluation in High Speed Rotating Machinery with the LCR Ultrasonic Technique," Proceedings of the 26th Turbo Machinery Symposium, Bailey, Jean C., Tech Ed., Sep. 16–18, 1997, pp. 143–149, Texas A&M University, Houston, Texas.

Bray, Don E., and Tang, W., "Evaluation Stress Gradients in Steel Plates and Bars with the LCR Ultrasonic Wave," Approximate Methods in the Design and Analysis of Pressure Vessels and Piping Components, Proceeding 1997 ASME Pressure Vessels and Piping Conference, W. J. Bees, Ed., Jul. 1997, , pp. 157–164, PVP–vol. 347, Orlando, FL.

Bray, D. E., Tang, W. and Grewal, D., "Ultrasonic Stress Evaluation in a Turbine/Compressor Rotor," Review of Progress in Quantitative NDE, Jul. 28–Aug. 2, 1996, pp. 1691–1697, Brunswick College, Brunswick, ME.

Tang, W., and Bray, D. E., "Stress and Yielding Studies Using Critically Refracted Longitudinal Waves," NDE Engineering Codes and Standards and Material Characterization, Proceedings 1996 ASME Pressure Vessels Piping Conference, Montreal, PQ, Jul. 1996, pp. 41–48, PVP–vol. 322, NDE–vol. 15, J. F. Cook, Sr., C. D. Cowfer, and C. C. Monahan, Eds.

Bray, D. E., Srinivasan, M., and Pathak, N., "Residual Stress Distributions in a Steam Turbine Disk using the LCR Ultrasonic Technique," Proceedings of the Seventh International Symposium of Nondestructive Characterization of Materials, Prague, Czech Republic, Jun. 19–22, 1995, pp. 317–324, A. Bartos, R. E. Green, Jr. And C. O. Ruud, Eds., Transtec.

Bray, D.E. and Junghans, P.G., "Application of the LCR Ultrasonic Technique for Evaluation of Post–Weld Heat Treatment in Steel Plates," NDE–vol.–13, NDE for the Energy Industry 1995, Proceedings The Energy Sources Technology Conference and Exhibition, 1995, pp. 63–71, Houston, Texas.

Bray, D.E. and Srinivasan, M., "The LCR Ultrasonic Technique for Stress Measurement and Material Characterization," Proceedings International Petroleum Industry Inspection III, Topical Conference, Jun. 1993, pp. 117–12, American Society for Nondestructive Testing, U.S.A.

Tang, W. and Bray, D.E., "Macro–Stress and Materials Characterization Studies in Composite by the LCR Ultrasonic Technique," Nondestructive Evaluation, PD–vol. 54, NDE–vol. 11, Jan./Feb. 1993, pp. 53–60, Proceedings 16th Annual Energy–Sources Technology Conference, Houston, TX,.

Pathak, N., Bray, D.E., and Srinivasan, M.N., "Detection of Stress in a Turbine Using the LCR Ultrasonic Technique," Serviceability of a Petroleum, Process and Power Equipment, PVP–vol. 239/MPC–vol. 33, Jun. 1992, pp. 1–3, Proceedings 1992 ASME Pressure Vessels Piping Conference, New Orleans, LA.

Junghans, P. and Bray, D., "Beam Characteristics of High Angle Longitudinal Waves Probes," NDE: Applications, Advanced Methods, Codes and Standards, PVP–vol. 216, NDE vol. 9, Jun. 1991, pp. 39–44, Proceedings 1991 Pressure Vessels and Piping Conference, San Diego, CA.

Chundu, S., Srinivasan, M., and Bray, D., "Residual Stress Measurement in Ductile Cast Iron Using The LCR Ultrasonic Technique," NDE: Applications, Advanced Methods, Codes and Standards, PVP–vol. 216, NDE vol. 9, Jun. 1991, pp. 49–54, Proceedings 1991 Pressure Vessels and Piping Conference, San Diego, CA.

Leon–Salamanca, T. and Bray, D.E., "Ultrasonic Measurement of Residual Stress in Steels Using Critically Refracted Longitudinal Waves (LCR)," Jun. 1990, pp. 271–278, Proceedings 1990 Spring Conference on Experimental Mechanics, Albuquerque, NM.

Bray, D.E., "Application of Critically Refracted Ultrasonic Waves for Petroleum Industry Inspection," Proceedings Petroleum Industry Inspection Technology, Topical, Jun. 1989, pp. 157–161, American Society for Nondestructive Testing, Houston, TX.

Bray, D.E., Leon–Salamanca, T., and Junghans, P., "Applications of the LCR Ultrasonic Technique for Evaluating Post Weld Heat Treatment in Steel Plate," in Streit, R., ed., Nondestructive Evaluation NDE Planning and Application, NDE 5, Jul. 1989, pp. 191–197, Proceedings 1989 Pressure Vessels and Piping Conference, Honolulu, HI.

Leon–Salamanca, T., Reinhart, E., Bray, D.E., and Golis, M., "Field Applications of an Ultrasonic Method for Stress Measurement in Structure," Apr. 1989, pp. 1484–1489, Boogaard, J. and Van Dijk, G., eds., Nondestructive Testing (Proceedings 12th World Conference), Amsterdam, The Netherlands.

Leon–Salamanca, T., and Bray, D.E., "Application of Ultrasonic P–Wave for Nondestructive Stress Measurement," Nov. 1985, Proceedings of the 11th World Conference on Nondestructive Testing, Las Vegas, NV.

Leon–Salamanca, T., and Bray, D.E., "Mean Travel–time for Zero–Force Determination in Railroad Rails Using P–Waves," Apr. 1985, Proceedings of the 15th Symposium on NDE, San Antonio, TX.

Bray, D.E. and Egle, D.M., "Field Tests on the Use of Ultrasonic Wave Velocity Changes to Detect Longitudinal Stress Variations in Railroad Rail," Conference on Nondestructive Techniques for Measuring the Longitudinal Force in Rails, Feb. 1979, FRA/ORD–80–50, Jun. 1980, Federal Railroad Administration/Association of American Railroad, Washington, D.C.

Bray, D.E. and Egle, D.M., "Residual Stress Measurement in Railroad Rail," Proceedings of a Workshop in Nondestructive Evaluation of Residual Stress, NTIAC–76–2, 1975, pp. 187–195, Nondestructive Testing Information Analysis Center, San Antonio, TX.

King, R.R., Birdwell, J.A., Clotfelter, W.N., Risch, E.R., and Bray, D.E., "Improved Methods for Nondestructive Measuring Residual Stress in Railway Wheels," Apr. 1973, pp. 91–105, Proceedings of the Ninth Symposium on NDE, San Antonio, TX.

Bray, Don E., "Fixing the Impedance Mismatch in Engineering Education," Mehl Honor Lecture, Keynote Address, Fall Conference, Oct. 11–19, 1999, The American Society for Nondestructive Testing, Phoenix, AZ.

Bray, Don E., "Application of Ultrasonic Stress Measurement to Engineering Components," Pres. No. 2Aea3, Invited presentation to 134th Meeting of the Acoustical Society of America, Dec. 2, 1997, San Diego, CA.

* cited by examiner

APPARATUS AND METHOD FOR ULTRASONIC STRESS MEASUREMENT USING THE CRITICALLY REFRACTED LONGITUDINAL ($L_{CR}$) ULTRASONIC TECHNIQUE

This application is a continuation-in-part of application Ser. No. 09/234,157, filed Jan. 19, 1999, which claims the benefit of Provisional application Ser. No. 60/094,684, Jul. 30, 1998.

BACKGROUND OF THE INVENTION

1. Technical Field

The present invention relates to an apparatus and method for non-destructive testing of stress within solid materials using the $L_{CR}$ ultrasonic technique. Specifically, the present invention relates to an improved technique and apparatus which provides a more accurate stress measurement in curved engineering components such as pressure vessels, tanks and piping.

2. Description of the Related Art

The non-destructive testing for stress in metals has long been recognized as an important method for evaluating metal components to predict both the failure location and rate, to identify stressed components prior to failure, and many other safety related considerations. Non-destructive testing is used extensively in a wide variety of industries including the aviation, automotive, petroleum, and chemical industries, and various construction and structural related fields. The use of non-destructive testing on specific components ranges from the testing of steel turbine blades in jet engines to steel support beams in bridges and other large structures. The benefit of non-destructive testing is self-evident. Components in use can be tested to determine the stress levels in the components without damaging or destroying the components.

Techniques such as x-ray diffraction and Barkhausen noise analysis have been successfully applied for nondestructive stress measurements. While the x-ray techniques are quite reliable in their measurements, they measure stress in only the top few angstroms of the surface, and the results may not be indicative of internal stresses. The Barkhausen method is based on small changes in magnetic permeability due to stress. Application of the Barkhausen method is limited to the surface and to electrical conducting materials. It has been available for a number of years, but has not been shown to give generally reliable results.

The $L_{CR}$ ultrasonic technique indicates stress through the acoustoelastic principle where small variations in strain affect the wave speed. By measuring the wave speed (or travel-time between known points) the change in stress can be calculated. Other material variations such as texture and temperature also affect the travel-time. The investigator using the $L_{CR}$ method must be aware of these other effects so that the best data indicative of stress variation is obtained.

The relationship of measured $L_{CR}$ wave travel-time change and the corresponding uniaxial stress is given by:

$$\Delta\sigma = \frac{E}{Lt_0}(t - t_0 - \Delta t_T)$$

where $\Delta\sigma$ is change in stress, E is Young's modulus, and L is the acoustoelastic constant for longitudinal waves propagating in the direction of the applied stress field, as given in Table 1. Travel-time change ($\Delta t$) is the measured travel-time (t) minus the reference travel-time ($t_o$). The reference travel-time $t_0$ is a property of the probe sensor spacing for an assumed stress free material.

TABLE 1

Typical values for acoustoelastic constant (L)

| Material | Load | L |
| --- | --- | --- |
| Pearlitic steel | Tension | −2.38 |
| | Compression | −2.45 |
| 4140 steel | Tension 2.25 MHz | −2.2 |
| | Tension 5 MHz | −2.36 |
| Clear acrylic-aircraft grade | Tension | −2.14 |

Temperature induced speed changes occur both in the material being investigated and in the probe material. The relationship of wave speed and temperature (dc/dT) is given by:

$$\frac{dc}{dT} = k_T \frac{m}{s - °C.}$$

where $k_T$ is the constant for a particular material, as given in Table 2.

TABLE 2

Temperature effects on wave speed

| Material | $k_T$ |
| --- | --- |
| PMMA | −2.3 |
| Pearlitic Steel | −0.55 |

The effect of temperature on travel-time will be $$\Delta t_T = \frac{d}{k_T \Delta T}$$

where d is the travel distance in the material and $\Delta T$ is the measured temperature change. Thus, as shown in Table 2, the temperature effect for PMMA is greater than that of the steel. Where data are collected under moderately uniform temperature conditions, the temperature effect, $\Delta t$, can be ignored. For large temperature variations, a suitable correction in the travel-time can be made.

Texture as typically encountered in cold-rolled plates and other structural shapes can have a significant affect on the wave speed. While the affect of texture on the $L_{CR}$ wave speed is less than that encountered by the shear waves often used in acoustic-birefringence stress measurements, there still is concern about the effects.

Special data collection procedures may be used to minimize the effects of texture. In many items where stress is a concern, the texture may be uniform throughout. In these cases, $L_{CR}$ travel-times taken with the probe always at the same orientation relative to the geometry of the item may be free of texture variation. In this case, the major effect may be stress. This has been found to be true for plates and welded structures. However, there is a need for more data on additional structures and shapes before this assumption may be more widely made.

Ideally, the $L_{CR}$ pulse is a true, nondispersive wave travelling at the longitudinal wave speed of the material. There are shape and material effects, however, that can cause dispersion of the wave. In many of these cases, the wave can still be used for stress measurement by the careful operator, and by choosing the proper probe.

Wave-guide effects are one of the most serious causes of dispersion, although they are easy to eliminate due to knowledge of the geometry of the test specimen. These effects occur in plates and pipes, which act as the waveguide, when the wavelength of the wave approaches some fraction of the thickness. Typically, when the ratio of plate thickness to wavelength is ten or above, there is no risk of any waveguide effect. Satisfactory results have been obtained with ratios of five.

Texture effects, discussed above, and grain boundary scattering also affect the pulse shape. Texture may be evaluated with a contact shear wave acting across the thickness. Grain boundary scattering may be evaluated with attenuation measurements also across the boundary. Data is still being collected to determine acceptable ranges for $L_{CR}$ stress measurement in light of these dispersive effects.

Choosing the proper reference location within the $L_{CR}$ pulse can enable the collection of reliable data. When the data are collected, a wave form is observed that crosses above and below a reference of zero. Typically, the second positive zero crossing at the first arrival of the pulse is used as this reference. In nondispersive conditions, this location is easy to identify at all pulse arrivals. Under dispersive conditions, however, identification may be more difficult. In difficult circumstances, identification can be aided by sliding a receiver probe along the travel path and observing the change of shape.

Ultrasonic stress measurement techniques have been developed in the past. Some use longitudinal waves, but they have not met with success due to the absence of a method for accurately controlling the coupling state between the probe and the item being inspected. Others use shear (SH) and/or Rayleigh waves which are well known to be less sensitive to stress than is the $L_{CR}$ wave.

Accordingly, a need exists for a non-destructive testing method and apparatus to accurately indicate the internal stresses of metal, particularly curved engineering components such as pressure vessels and pipes. The method and apparatus should accurately control the coupling state between the probe and the item being inspected and take into account or avoid various interference factors, thus providing accurate and reliable stress measurements. Further, the method should be useful for both flat materials and curved engineering components, such as pressure vessels and pipes.

SUMMARY OF THE INVENTION

The $L_{CR}$ ultrasonic technique is a unique nondestructive method for evaluating stress levels and other mechanical property variations in various engineering components, structures and materials. The inspection is accomplished with a newly designed apparatus incorporating an $L_{CR}$ ultrasonic probe, a variable force application device and a mechanism for attachment of the probe to the item being evaluated.

A novel feature of the $L_{CR}$ technique is the ability to apply an even, linear variable force to the interface of the $L_{CR}$ probe and the item being inspected. The force is equal at the interfaces between the specimen, the transmitting probe and one or more receiving probes since the single force applicator is located equidistant between the interfaces. Further, the magnitude of the force can be established through the use of a measurement device such as a pressure gauge. This feature enables the reliable and repeatable measurement of the $L_{CR}$ travel-time changes with at most a 0.0004% error.

The $L_{CR}$ probe technique operates in a send-receive mode, using a transmitting probe and at least one or more receiving probes. Both the transmitting and receiving probes are on one side of the material. The $L_{CR}$ wave is excited at approximately the first critical angle +/−2 degrees for the probe wedge and specimen combination. For curved components and surfaces, a rotatable wedge coupled to the transmitting and receiving probes enables proper interface with the curved component. The pulse travels from the transmitting probe to the receiving probe(s) as a bulk, critically refracted longitudinal (LCR) wave and encounters the stress effect in its path. Since the $L_{CR}$ wave propagation is just beneath the surface, the stress and other material property variations within its penetration path affect the speed of the wave. Surface conditions have little affect on the wave travel. Moreover, frequency variation and analysis techniques may establish stress and other property gradients existing below the surface.

A working prototype $L_{CR}$ stress measurement apparatus has been developed. The disclosed embodiment of the $L_{CR}$ stress measurement apparatus and process has been demonstrated in lab and field applications in railroad rail, welded steel plates, a turbine disk and blades, a compressor rotor, rolled aluminum plates, rolled steel plates, titanium plates and ductile cast iron samples.

The present $L_{CR}$ ultrasonic technique and apparatus can also be used to perform nondestructive testing of stress levels and other mechanical property variations in curved engineering components such as pressure vessels and pipes. Longitudinal wave speeds, even in curved surfaces, are related to stress through the acoustoelastic effect. The inspection is accomplished with a newly designed apparatus incorporating $L_{CR}$ ultrasonic probes coupled with rotatable polystyrene wedges designed for interfacing with curved surfaces, a variable force application device and a mechanism for attachment of the probe to a curved surface.

The present $L_{CR}$ technique and apparatus can excite and detect a longitudinal wave travelling across the chord of a curved surface, in the longitudinal direction and at various angles between. The rotatable wedges allow the transmitting and receiving probes to interface with the surface of the curved structure at the appropriate wave propagation angle and direction. Generally speaking, the requirement for the contact area during the stress measurement inspection is that it must be free of dirt, water, oil, scale and other loose debris that can affect probe wedge contact with the specimen. Ordinary metal scale does not affect the $L_{CR}$ data, provided that it is smooth and tightly adhered to the plate or pipe.

Ultrasonic instrumentation required for collecting $L_{CR}$ data includes a typical commercial pulser/receiver and a computer data acquisition system with a high speed digitizing board, or a digital oscilloscope. Suitable virtual instruments such as Labview are preferable for data interpretation. Arrival-time resolution of 0.25 ns or better is needed for the instrumentation. The board and suitable software can be conveniently fitted into expansion slots on a PC or Laptop computer. Since temperature can affect the travel-time data, temperature data also may be collected during the test. Stress changes may then be calculated from the observed differences in wave travel times using the appropriate formulas. Judgement of stress change or stress fields would be based on the deviation of the observed travel time from some previously established zero stress norm. Since material texture significantly affects the wave speed, the zero stress norms may be established with prior data on the material being inspected, or by comparison with a known stress free region in the material.

One embodiment of the invention would allow the probe assembly to be integrated with a remote control transport device that would allow remote stress measurements to be taken and the data transmitted to a receiving system via wireless means. This embodiment would allow the collection of data in locations or physical environments which are difficult to access or pose a risk of danger or injury to the user.

The distinct advantage of the $L_{CR}$ ultrasonic technique utilized by the apparatus described herein is that the rigid frame with rotating probe wedges and variable force application feature enables the accurate collection of wave travel-time data in curved components. This data enables the determination of stress variations in multiple planes of flat or curved materials at various depths.

The above, as well as additional features and advantages of the present invention, will become apparent in the following written detailed description.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE DRAWINGS

Figure 1:
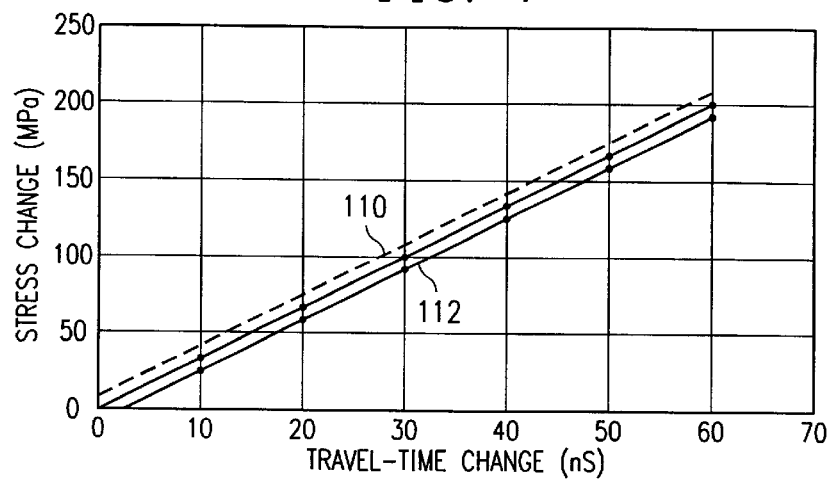
FIG. 1 illustrates the typical relationship of stress change with travel-time change for steel. Outer lines show variations with ±3 ns system repeatability.

FIG. 1 shows the nominal relationship of stress variation and $L_{CR}$ wave travel-time for steel. The outer lines 110, 112 show the range for an expected measurement variation of ±3 ns. Typical stress induced travel-time changes for $L_{CR}$ waves are small, at approximately 0.01%. Thus, travel-time variations caused by the testing procedure should be reduced to at least one tenth of that level for the desired stress resolution.

Testing procedure variations can arise from the instrumentation and the repeatability of the ultrasonic probe system. Instrumentation capable of measuring arrival times of a least a nanosecond is needed for good resolution. Further, probe repeatability at a designated location should be in the 2 to 3 ns range, or better.

Figure 2A:
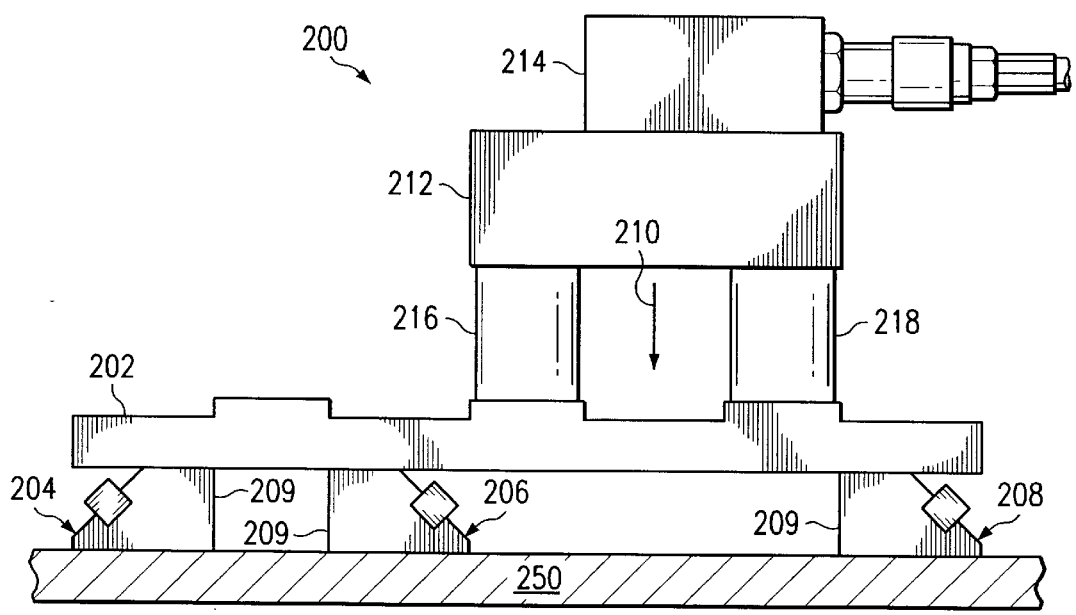
FIG. 2a is a schematic of one embodiment of the invention.

Referring to FIG. 2a, a probe assembly 200 is shown comprising a rigid member or probe frame 202 which is constructed of a rigid material such as aluminum, steel or a ceramic, a transmitting probe 204 which initiates the signal through the test sample 250, and one or more receiving probes 206, 208. A force 210 is applied at a point equidistant between the two receiving probes 206, 208 via a hydraulic ram or, in other embodiments of the invention including, but not limited to, an electromagnetic actuator, weights or pneumatic pressure. This provides uniform couplant distribution at the interface between the test specimen 250 and probes 204, 206, 208.

Figure 2B:
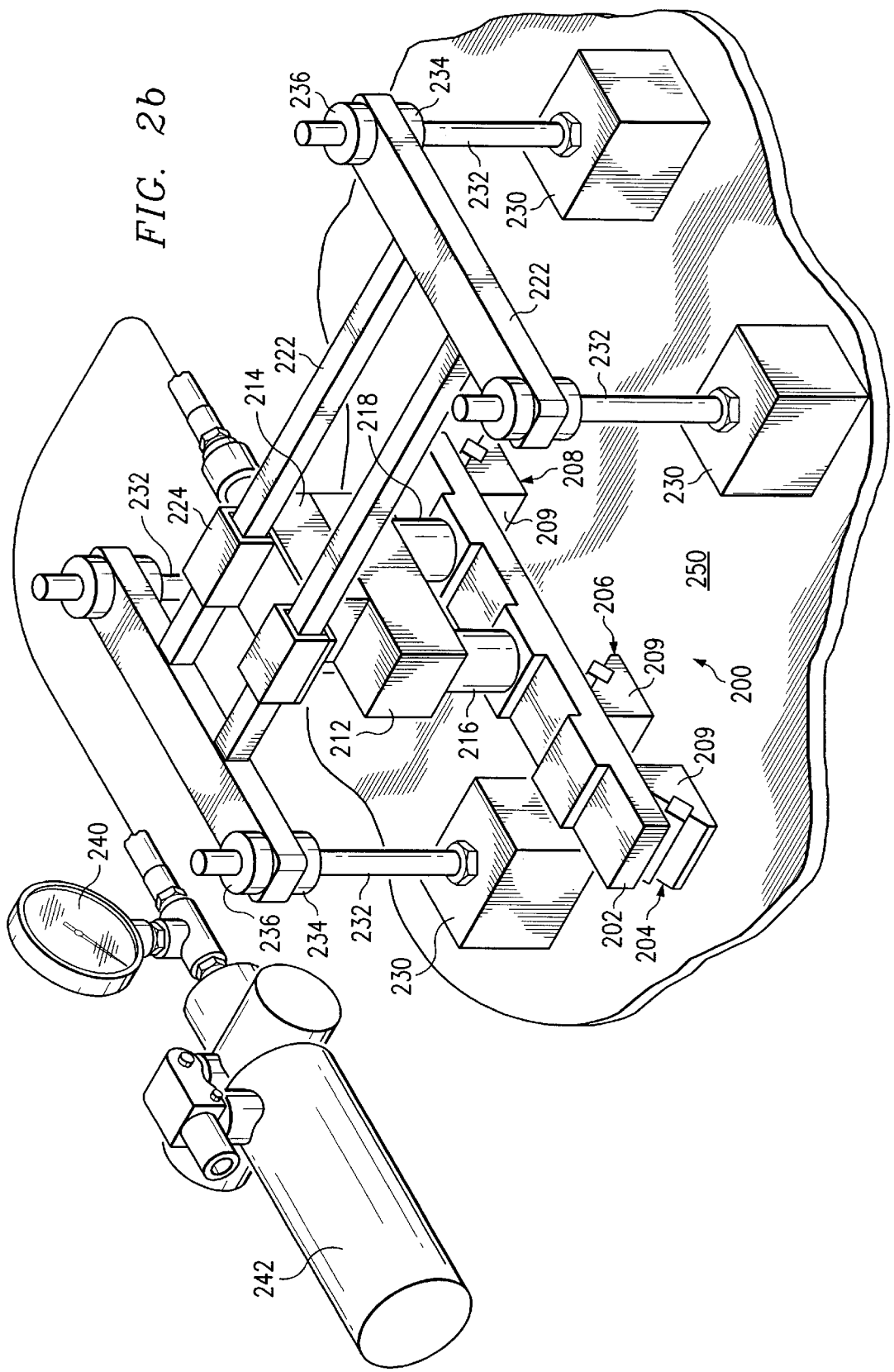
FIG. 2b is a perspective view of one embodiment of the invention.

FIG. 2b depicts in further detail the probe assembly 200 comprising an aluminum probe frame 202, a transmitting probe 204, and two receiving probes 206, 208. At the contact between the receiving probes 206, 208, and the surface of the tested material 250 are shown wedge-shaped polystyrene pads 209 which are preferable due to their ultrasonic properties and geometrical shape. In the depicted embodiment, a force 210 is transmitted to the probe assembly by way of a hydraulic piston or ram 214, which is driven by a hydraulic pump 242. Piston 214 is shown connected to a rigid block 212. The rigid block 212 is placed over two rigid posts 216, 218, which transmit force 210 to the aluminum probe frame 202. The piston 214 in turn abuts and transmits an opposite force to the load frame 222, comprised of various support members, by way of a sliding plate bracket 224 or other connecting means. Alternatively, the piston 214 can be attached to the sliding plate bracket 224 and be physically placed on top of the rigid block 212. The load frame 222 is secured to four posts 232 by upper collars 236 and lower collars 234. These four posts 232 are attached to four magnets 230 (three of which are shown), which secure the entire assembly to the test sample 250. Other devices such as vacuum and mechanical constraints can be used. Such devices are necessary when the test sample 250 is, for example, aluminum, ceramic, or of an unusual geometry for which a magnetic interface would not be possible or appropriate.

The hydraulic ram 214 is fitted on the top of the probe frame 200 to provide a variable force at the couplant interface between the probes 206, 208 and the test sample 250. The force line 210 of the ram 214 is midway between the two receiving probes 206, 208, resulting in uniform pressure distributed on these interfaces between the test specimen 250 and probes 206, 208. Pressure on the ram 214 is indicated by a pressure gauge 240 on hydraulic pump 242. In one embodiment, the hydraulic pump 242 can also be mounted directly on the sliding plate bracket 224.

A typical setup for one embodiment of the invention involves first positioning the lower collars 234 on the posts 232 so that the tops of the collars 234 are about 159 mm (6.25 in.) from the plate 250. Next, the load frame 222 is placed on the posts 232 and the upper collars 236 are secured leaving about 1 mm of clearance between the upper collar 236 and the frame 222. The entire assembly is then placed in position on the plate 250 and the magnets 230 are activated. After assuring that the contact areas on the probes 206, 208 and the plate 250 are clean, couplant is applied to the probe contact areas. The probe assembly 200 is then inserted and the sliding plate bracket 224 is positioned over the ram 214. Hydraulic pressure is then applied via the hydraulic pump 242 in order to secure the probe assembly 200 in place. The higher the pressure achieved the more accurate are the results. Accurate results have been obtained using the embodiment illustrated in the range of 200 to 400 psi. Obtaining the higher pressures required for achieving small travel-time variations is dependent on good magnetic coupling or other suitable interface. This requires that the magnets 230 be firmly placed on the plate or sample 250, and that the load frame 222 be able to move freely on the posts 232. If this condition is not met, the magnets 230 will pull loose from the plate when the piston force is applied. Some adjustment of the magnet 230 position and the collar 234, 236 placement is often needed to achieve good quality data.

Figure 2C:
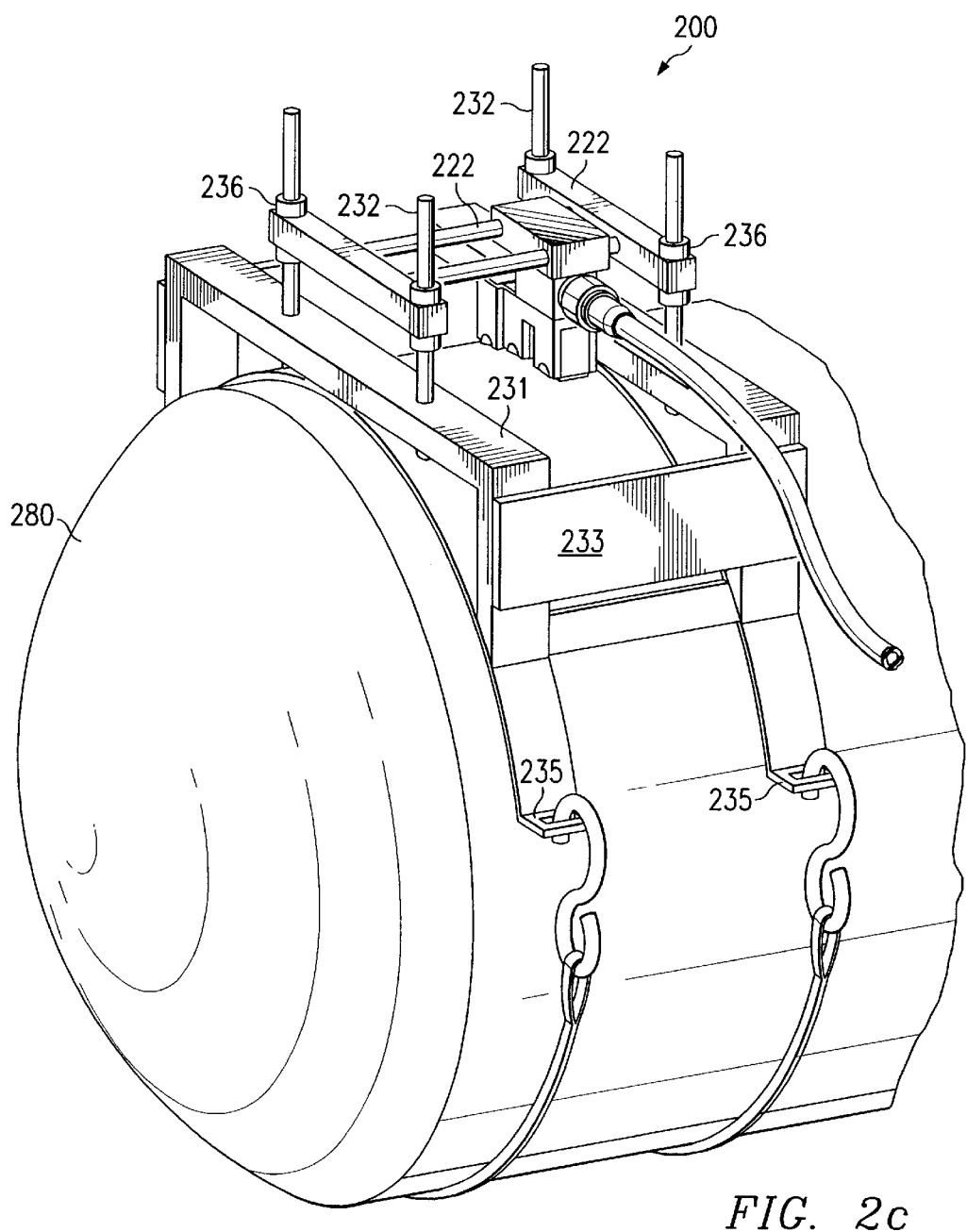
FIG. 2c is a profile view of one embodiment of the invention attached to a curved engineering component.

FIG. 2c shows another embodiment of the probe assembly 200 clamped to a curved test specimen 280 via clamp rings 235. The probe frame 202 is modified by the addition of reinforcing bars 231 and 233 which are attached to clamp rings 235 and to the frame assembly 202 via rigid posts 232.

Figure 2D:
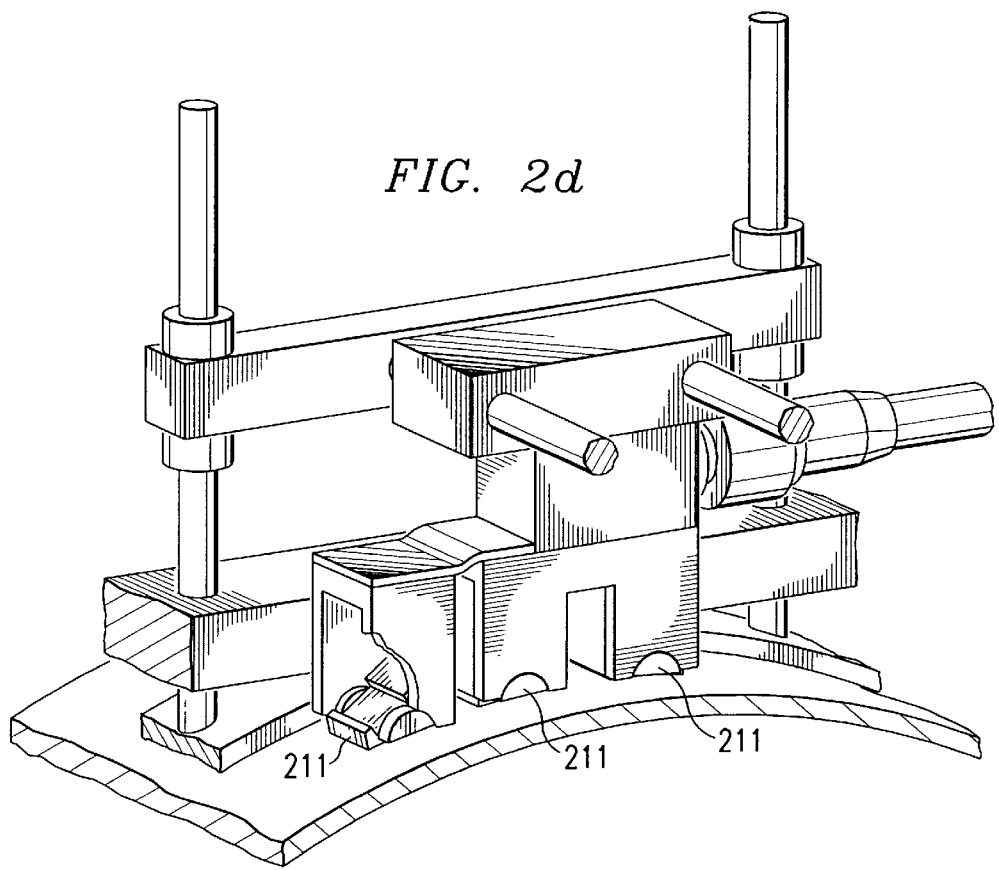
FIG. 2d is a perspective view of one apparatus embodiment with rotatable wedges which enable placement of the invention on curved engineering components.

FIG. 2d depicts in further detail the rotatable, wedge-shaped polystyrene pads 211 which allow the probe assembly 200 and, in particular, the transmitting probe 204 and receiving probes 206, 208 to be tangentially coupled against the surface of the curved test specimen 280 and properly oriented to send and receive the wave pulse across the chord length 285 of the curved test specimen 280. The ability of the wedge-shaped polystyrene pads 211 to rotate freely in both the axial and longitudinal planes tangential to the contact point between the wedge-shaped polystyrene pads 211 and the curved engineering test specimen 280, allows for the probe assembly 200 to be attached to myriad curved engineering components 280 with various diameters and angular arcs. Likewise, it provides uniform couplant distribution at the contact point between the wedge-shaped polystyrene pads 211 and the surface of the curved engineering test specimen 280 as previously discussed.

Figure 2E:
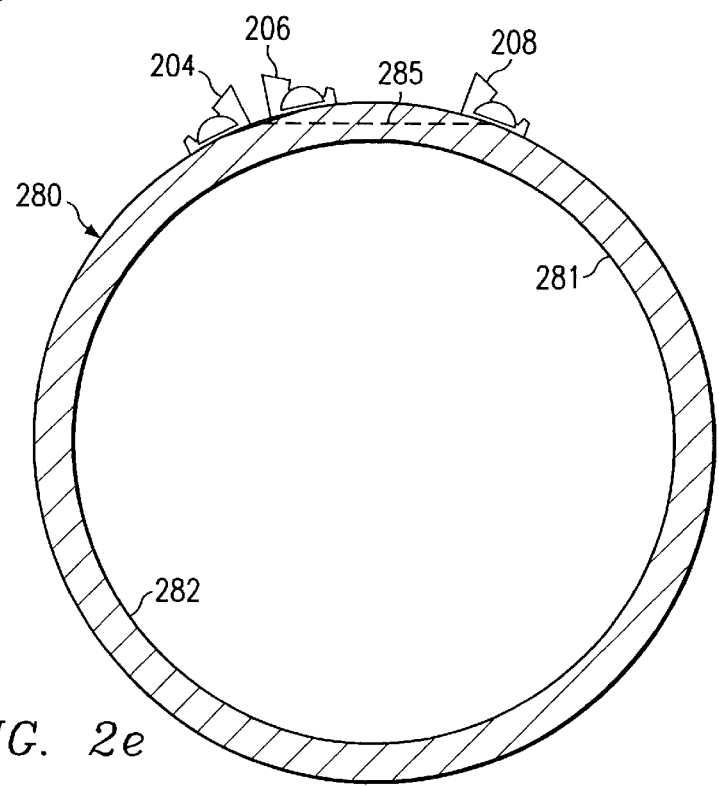
FIG. 2e is a profile view of the apparatus embodiment which depicts the proper orientation of the transmitting probe and one or more receiving probes across the chord length of a curved engineering component for reliable data collection.

FIG. 2e shows a profile view of the curved test specimen 280 with an interior surface 281 and exterior surface 282. The transmitting probe 204 and receiving probes 206, 208 are shown oriented to emit and receive a wave pulse across the chord length 285 of the curved test specimen 280.

Figure 2F:
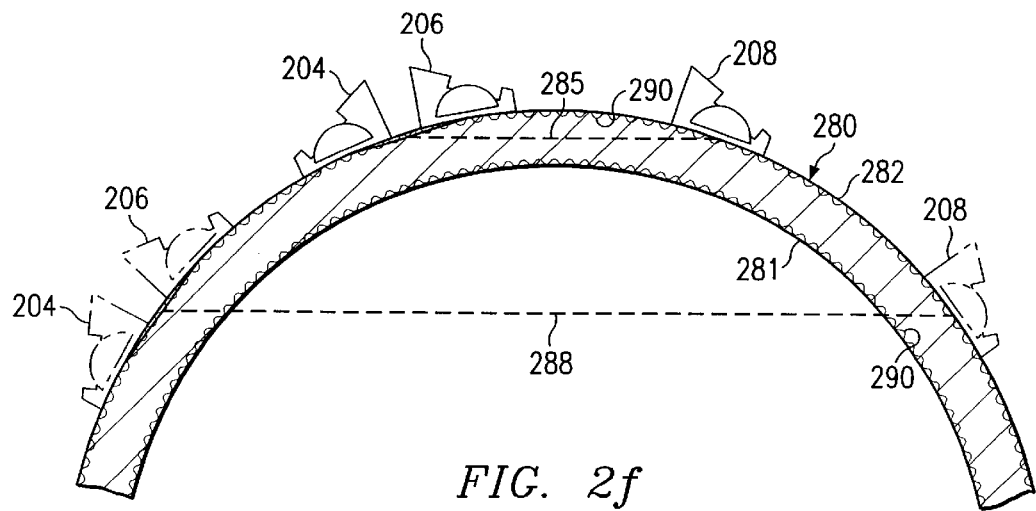
FIG. 2f is an exploded view of one embodiment providing further detail of the proper orientation of the transmitting probe and one or more receiving probes across the chord length of a curved engineering component to avoid dispersion of the pulse wave due to nonuniform boundary textures.

FIG. 2f is an exploded profile view of the curved test specimen which shows one possible placement of the transmitting probe 204 and receiving probes 206, 208 which allows for the emission and receipt of a pulse wave across chord length 285. In contrast, placement of the transmitting probe 204 and receiving probes 206, 208 in a geometric position which results in the chord length 288 passing into the area defined by interior surface 281 may result in dispersion of the pulse wave and erroneous, compromised data. Likewise, placement of the transmitting probe 204 and receiving probes 206, 208 where a part of the chord length 285 passes through nonuniform boundary textures 290 located within the interior surface 281 and exterior surface 282 may result in dispersion and scattering of the pulse wave and erroneous, compromised data.

The embodiments illustrated in FIGS. 2a, 2b, 2c and 2d show a single transmitting probe 204 and two receiving probes 206, 208. Use of two receiving probes 206, 208 allows for elimination of the temperature effects on the stress measurements. In applications where temperature effects are nominal, the same principals of the invention can be applied by using a single transmitting probe 206 and a single receiving probe 208, with a force applied equidistant between the two for uniform couplant distribution as previously described herein.

Further, FIGS. 2a and 2b illustrate an embodiment of the invention used for testing a flat, linear materials. FIGS. 2c and 2d depict an embodiment of the invention used for testing pipes, pressure vessels and other curved engineering components. Minor adjustments to the interface between the illustrated embodiments of the probe assembly 200 and test materials 250, 280 can be made when stress measurements of materials involving complex geometry or shapes are being collected.

Since the $L_{CR}$ wave travels underneath the test material surface at bulk, longitudinal wave speed, it will be the first arriving wave at receiving probe(s) along its path. The change in travel-time of the wave will be indicative of the stress change. The stress induced travel-time changes are small, however, and very accurate and precise methods are required to accomplish this measurement. The following is a description of a suitable data collection method using a high speed digitizing card and an appropriate interface program on a personal computer.

Figure 3:
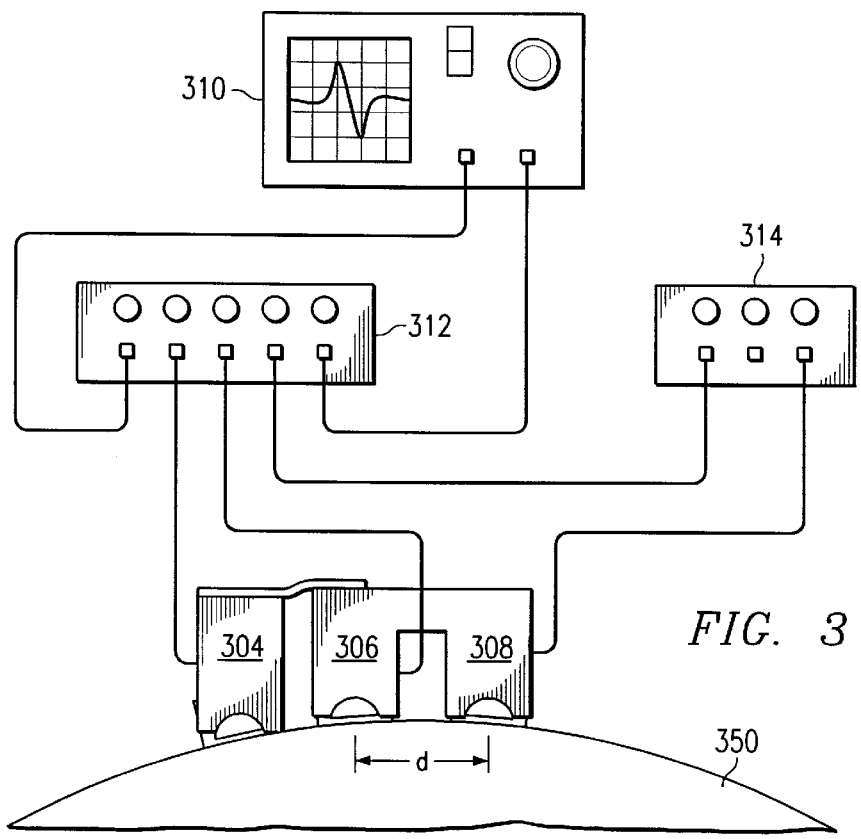
FIG. 3 is a schematic of one embodiment of the data collecting system of the invention.

A variety of measurement systems may be used for collecting $L_{CR}$ data. Referring to FIG. 3, a typical system includes a commercial ultrasonic pulser/receiver as well as an oscilloscope and the $L_{CR}$ transmitting probe. The specimen or test sample 350 is again shown in contact with a transmitting probe 304 and two receiving probes 306, 308. Also shown is a computer or oscilloscope 310, the pulser/receiver 312, and a preamp 314. The oscilloscope 310 may be a stand-alone unit, such as LeCroy digital oscilloscope, or a high speed digitizing board (Gage Scope 265) inserted in a personal computer. If the high speed digitizing board is used, the computer 310 must be fitted with suitable software, such as Lab View, so that the travel-time measurements can be made. The instrument must be able to resolve arrival-times in the 0.1 to 0.01 ns range.

The pulse originates as the pulser/receiver 312 emits a spike that excites the oblique sending transmitting probe 304. The pulse travels as a $L_{CR}$ wave through a short distance in the material, and is received by the two receiving probes 306, 308 which are arranged in tandem. In some cases, a preamplifier 314 is inserted in the connection to the second receiving probe 308 to increase the signal amplitude.

Wave travel time comparison is made between a stressed test specimen and a substantially identical unstressed specimen. The baseline stress value in the unstressed specimen is dependent upon the pulse wave travel time between the transmitting probe and receiving probe(s) which in turn is related to the spacing between the transmitting probe 304 and receiving probes 306, 308. The probe spacing when conducting wave travel time measurements on the stressed specimen should be substantially similar to the probe spacing applied to the unstressed specimen when collecting baseline wave travel time measurements. For example, a probe spacing (d) of 152.4 mm (6 in.) between the first receiving probe 306 and the second receiving probe 308 yields an initial travel time in a stress-free state between the two tandem receiving probes 306, 308 of about 25.7 μs. With an instrumentation resolution of 0.1 ns, the system is capable of measuring travel-time changes of approximately 0.0004%.

The time resolution (precision) of the high-speed digitizing card is a function of the sampling rate. Lab View enables the presentation of a typical oscilloscope screen on the computer monitor. While the presentation is similar to that of an oscilloscope, there are significant differences that need to be discussed.

The parameter START on LabView is analogous to DELAY on a typical oscilloscope or ultrasonic flaw detector. NUMBER represents the expansion of the time base of the display. The larger the positive value in START, the later the start of the display after the trigger. The smaller the NUMBER value, the fewer points displayed, and the greater the time expansion of the time-base (i. e. smaller µs/div). The SAMPLING RATE represents the firing rate of the card, which is associated with the maximum time resolution of the system. Note that for dual channel operation, the ACTUAL SAMPLING RATE per channel is one-half of the maximum SAMPLE RATE. POINTS (lower, left corner of screen) describes the total number of points displayed on the screen.

Higher precision will be achieved when using Lab View if all data are collected in single channel mode, using Channel A. In dual channel mode, the higher speed sampling rate is divided between the two channels so that the actual sampling rate is one half of the peak. In single channel mode, the actual sampling rate is the maximum. A higher speed board than the one used here could give satisfactory performance in dual channel mode.

Figure 4:
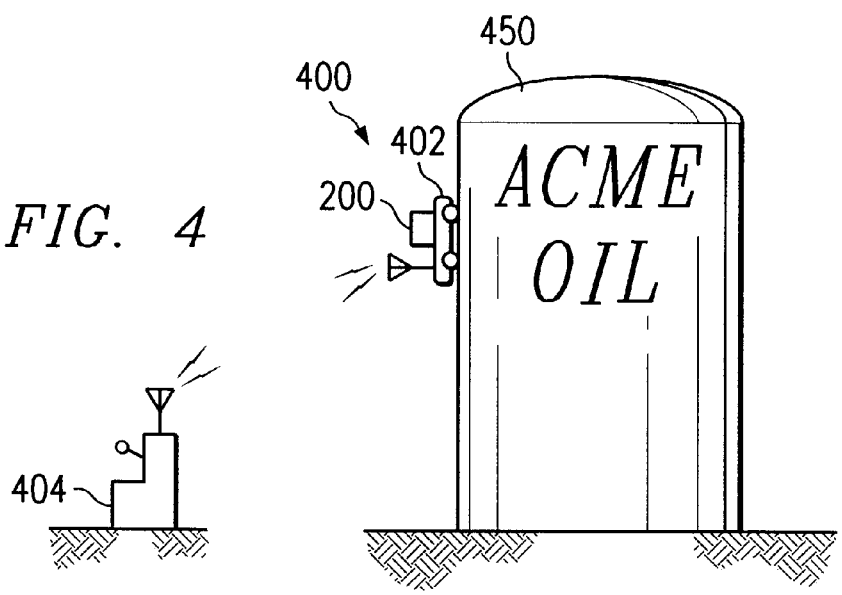
FIG. 4 shows one embodiment of the invention integrated with remote transport means and wireless data transfer to a remote receiving station for processing.

FIG. 4 illustrates one embodiment of the probe assembly 200 integrated with a remote controlled transport 400 consisting of a movable wheeled vehicle 402. The probe transport 400 may have magnetized wheels which allow the probe transport 400 to travel in both horizontal and vertical directions on metallic engineering components such as a petroleum storage tank 450. The probe transport 400 is guided via radio signals from remote station 404. Likewise, the probe assembly 200 is remotely actuated with the measured data transmitted and received by remote station 404 for storage of the data. The remote station 404 may also be integrated with a computer or oscilloscope 310, a pulser/receiver 312, and a preamp 314 so that the measured data may be processed at the remote station 404 location.

While the invention has been particularly shown and described with reference to the several embodiments, it would be understood by those skilled in the art that various changes in form and detail may be made therein without departing from the spirit and scope of the invention.

I claim:

1. An apparatus for determining the stress in a material comprising:
   (a) a frame coupled to the outside surface of a curved test specimen, and having a transmitting probe, wherein said transmitting probe may emit critically refracted ultrasonic waves, and wherein said waves are insensitive to a material thickness of said test specimen;
   (b) at least one receiving probe attached to said frame wherein said probes are rotatable to said frame; and
   (c) means for applying an equal contact force to said probes.

2. The apparatus of claim 1 wherein the means of applying an equal contact force comprises a hydraulic ram.

3. The apparatus of claim 1 wherein the means of applying an equal contact force comprises an electromagnetic actuator.

4. The apparatus of claim 1 further comprising:
   (d) a data collection means for measuring and processing output data from said at least one receiving probe.

5. The apparatus of claim 6 wherein the data collection means comprises an oscilloscope.

6. The apparatus of claim 6 wherein the data collection means comprises a personal computer.

7. The apparatus of claim 1 wherein there are two receiving probes and the means for applying an equal contact force is positioned equidistant between said receiving probes.

8. The apparatus of claim 1 further comprising:
   (d) a remote controlled wheeled transport; and,
   (e) a remote data collection means.

9. A method for measuring stress in a material comprising the steps of:
   (a) placing at least one transmitting probe in forced contact with the outside of a curved test specimen, wherein said transmitting probe is rotatable;
   (b) transmitting a critically refracted ultrasonic wave through the curved test specimen, wherein said waves are insensitive to a material thickness of said test specimen;
   (c) measuring the received ultrasonic wave at at least one receiving probe positioned on the outside of said specimen, wherein said receiving probe is rotatable; and,
   (d) correlating the measured ultrasonic wave to a calculated stress in the metal, wherein the forced contact comprises applying an equal force to both said transmitting and receiving probes.

10. The method of claim 9 wherein the forced contact of step (a) is accomplished with a hydraulic ram fixed to the curved surface of the material by magnets.

11. The method of claim 9 wherein the forced contact of step (a) is accomplished with a hydraulic ram placed in contact with said probes and fixed to the curved surface of the material by a mechanical constraint.

12. The method of claim 9 wherein the forced contact of step (a) is accomplished with a hydraulic ram placed in contact with said probes and fixed to the curved surface of the material by vacuum constraints.

* * * * *